US00PP24657P3

(12) United States Plant Patent
Olesen

(10) Patent No.: US PP24,657 P3
(45) Date of Patent: Jul. 22, 2014

(54) FLORIBUNDA ROSE PLANT NAMED 'POULCAS040'

(50) Latin Name: ***Rosa* hybrid**
Varietal Denomination: Poulcas040

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 91 days.

(21) Appl. No.: 13/507,026

(22) Filed: May 31, 2012

(65) Prior Publication Data

US 2013/0326757 P1 Dec. 5, 2013

(51) Int. Cl.
*A01H 5/00* (2006.01)

(52) U.S. Cl.
USPC ..... Plt./143; Plt./101; Plt./141

(58) Field of Classification Search
USPC ..... Plt./101, 141, 143
See application file for complete search history.

*Primary Examiner* — Susan McCormick Ewoldt

(57) ABSTRACT

A new garden rose plant of the compact floribunda rose class which has abundant, yellow and orange flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas040'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulcas040', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow and orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas040' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcas040' was selected in the spring of 2005 by the inventor as a single plant from the progeny of the aforementioned hybridization.

Asexual reproduction of 'Poulcas040' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcas040' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas040'. Specifically illustrated in the drawing are flowers at various stages of development, flower in parts, leaves, and stems. Plants illustrated are 2 years of age.

DETAILED DESCRIPTION OF THE VARIETY

The following is a description of 'Poulcas040', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulcs012', U.S. Plant Pat. No. 16,143 are compared to 'Poulcas040' in Chart 1.

CHART 1

| | 'Poulcas040' | 'Poulcs012' |
|---|---|---|
| Petalage | 40 petals total, 15 to 25 of which are petaloids. | 30 to 35 petals under normal conditions with 10 petaloids. |
| Flower Diameter | 65 to 90 mm. | 53 mm. |
| General Tonality of Flower Color | Open flowers are Yellow Group 10B, Yellow-Orange Group 19B, and Red Group 43C distinctly. Tonality changes to Red Group 46C and Yellow Group 11D as the flower ages. | On open flower Yellow Group 4D. No change in the general tonality at the end of the tenth day. |

FLOWER AND FLOWER BUD

Blooming habit: Continuous.

Flower bud:

*Size*.—Upon opening, 30 mm in length from base of receptacle to end of bud. Bud diameter is 20 mm.

*Bud form*.—Urceolate.

*Bud color*.—As sepals divide, petals are Yellow-Green Group 150C, Yellow Group 1B, and Red Group 42B.

*Sepal inner surface*.—Color: Yellow-Green Group 145B. Weak anthocyanin the color of Greyed-Orange Group 173A. Surface: Strong pubescence observed.

*Sepal outer surface*.—Color: Yellow-Green Group 144A, with strong anthocyanic pigments the color of Greyed-Red Group 178A. Texture: Rough with many stipitate glands.

*Sepal shape*.—Apex: Cirrhose. Base: Flat at union with receptacle.

*Sepal margin*.—Margins have moderate foliaceous appendages on three of the five sepals.

*Sepal size*.—25 mm long by 12 mm wide.

*Receptacle*.—Texture: Smooth. Shape: Funnel shaped. Size: 7 mm (height) and 7 mm (wide). Color: Yellow-Green Group 144A.

*Peduncle*.—Length: 2 to 3 cm. Diameter: 3 to 4 mm. Color: Yellow-Green Group 144A with strong intonations of Greyed-Red Group 178A.

*Pedicel*.—Surface: Rough with many small prickles and stipitate glands. Length: 30 to 40 mm. Diameter: 3 mm on average. Color: Yellow-Green Group 144A with strong anthocyanic pigments the color of Greyed-Red Group 178A observed. Strength: Strong.

Flower bud development: Flower buds are borne in clusters of 5 to 7 flower buds per stem, resembling a corymb.

Flower bloom:

*Fragrance*.—Moderate floral scent.

*Duration*.—The blooms have a duration on the plant of approximately 7 to 10 days. Petals fall cleanly away from plant after flowers have fully matured.

*Size*.—Flower diameter is 65 to 90 mm when open. Flower depth is 30 mm.

*Flower shape*.—General shape is a classic hybrid tea with a high center upon opening.

*Shape of flower, side view*.—Upon opening the upper portion is flat. The lower portion is a flattened convex. After opening, the upper portion is flattened convex, while the lower portion is a flattened convex.

Petalage: Under normal conditions, flowers have 40 petals total, 15 to 25 of which are petaloids.

Petal color:

*Upon opening, outer petals*.—Upper and lower surface are Yellow Group 8D with marginal intonations of Orange Group N34C blended with Red Group 42B.

*Upon opening, inner petals*.—Upper surface is Yellow Group 12A with marginal intonations of Orange Red Group 25B. The lower surface is Yellow Group 11A with light marginal intonations of Yellow-Orange Group 16B.

*Basal petal spots*.—Upon opening, the lower and upper surface is Yellow Group 6C.

*After opening, outer petals*.—The upper surface is Yellow Group 10B blending with Red Group 39B towards the margin. The margins are Red Group 41A. The lower surface is Yellow Group 10C with the margins becoming a mixture of Red Group 39B and 37A.

*After opening, inner petals*.—The upper surface is Yellow Group 10B splashed with Orange Group 27A. The lower surface is Yellow Group 10B.

*Basal petal spots*.—After opening, there is no distinctive coloration at the petal base.

General tonality: Open flowers are Yellow Group 10B, Yellow-Orange Group 19B, and Red Group 43C distinctly. Tonality changes to Red Group 46C and Yellow Group 11D as the flower ages.

Petals:

*Petal reflex*.—Strong reflexation.

*Margin*.—Entire and uniform. Medium undulations of margin observed.

*Shape*.—Generally Ovate. Apex shape: Rounded. Base shape: Rounded.

*Size*.—Variable. The inner petals are 30 mm (l)×27 mm (w). The outer petals are 40 mm (l)×45 mm (w).

*Texture*.—Smooth.

*Thickness*.—Average.

Petaloids:

*Quantity*.—15 to 25.

*Shape*.—Irregular and asymmetric. The apex is acute. The base is rounded.

*Color*.—Upper surface is Yellow Group 12A with marginal intonations of Orange Red Group 25B. The lower surface is Yellow Group 11A with light marginal intonations of Yellow-Orange Group 16B. The basal portion of the lower and upper surface is Yellow Group 6C.

Reproductive organs:

*Pollen*.—Color: None observed.

*Anthers*.—Size: 2 mm in length. Color: Yellow Group 11A. Quantity: 55 on average.

*Filaments*.—Color: Yellow-Orange Group 14A. Length: 6 mm.

*Pistils*.—Length: 5 mm. Quantity: 45 on average.

*Stigmas*.—Inferior in location relative to the length of the filaments and the height of the anthers. Color: Greyed-Yellow Group 160B.

*Styles*.—Color: Green-White Group 157A.

*Hips*.—None Observed.

PLANT

Plant growth: Upright. Plants are 55 cm in height, and 45 cm wide.

Stems:

*Color*.—Juvenile growth: Yellow-Green Group 144B with anthocyanin the color of Greyed-Red Group 182A. Mature growth: Yellow-Green Group 146B.

*Length*.—On average, canes are 40 cm from the base of the plant to the flowering portion.

*Diameter*.—5 mm.

*Internodes*.—On mature canes, there is an average distance of 35 mm between nodes.

*Surface texture*.—Young wood: Rough with many small prickles. Older wood: Rough with many small prickles.

Long prickles:

*Incidence*.—12 prickles per 10 cm of stem.

*Size*.—Average length of prickles on mature stems is 7 mm.

*Shape*.—Upper portion is linear. Lower portion is concave.

*Color*.—Juvenile prickles: Greyed-Red Group 181A. Mature prickles: Greyed-Yellow Group 161C.

Plant foliage: Normal number of leaflets per leaf in the middle of the stem is 7 leaflets.

*Compound leaf*.—150 mm (l)×120 (w).

*Quantity*.—3 leaves per 10 cm of stem on average.

*Color of juvenile foliage*.—Upper side: Yellow-Green Group 144A. Lower side: Yellow-Green Group 144B with strong anthocyanic pigments the color of Greyed-Purple Group 187A.

*Color of mature foliage*.—Upper side: Yellow-Green Group 147A. Lower side: Yellow-Green Group 146B.

Plant leaves and leaflets:

*Stipules*.—Size: 12 mm in length. Width is about 5 mm. Quantity: 2 per compound leaf. Shape: Linear, slightly broad based with outward extending apices. Margins: Finely serrated with many stipitate glands. Color: Yellow-Green Group 146A.

*Petiole*.—Length: 15 mm. Diameter: 2 mm.

*Upper surface*.—Color: Yellow-Green Group 144A.

*Lower surface*.—Color: Yellow-Green Group 144B. Observations: Numerous stipitate glands and small prickles observed.

*Rachis*.—Length: 65 mm. Upper surface: Color: Yellow-Green Group 144A.

*Lower surface*.—Color: Yellow-Green Group 144B. Observations: Numerous stipitate glands and small prickles observed.

*Leaflet*.—Edge: Serrated. Size: Average size of the terminal leaflet on normal leaves is 70 mm in length by 40 mm wide. Shape: Generally elliptic. Base: Rounded. Apex: Cuspidate. Texture: Smooth. Thickness: Average. Arrangement: Odd pinnate. Venation: Reticulate. Glossiness: Very Glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the compact floribunda rose class named 'Poulcas040', substantially as illustrated and described herein, due to its abundant yellow and orange flowers, disease resistance, and extended period of bloom.

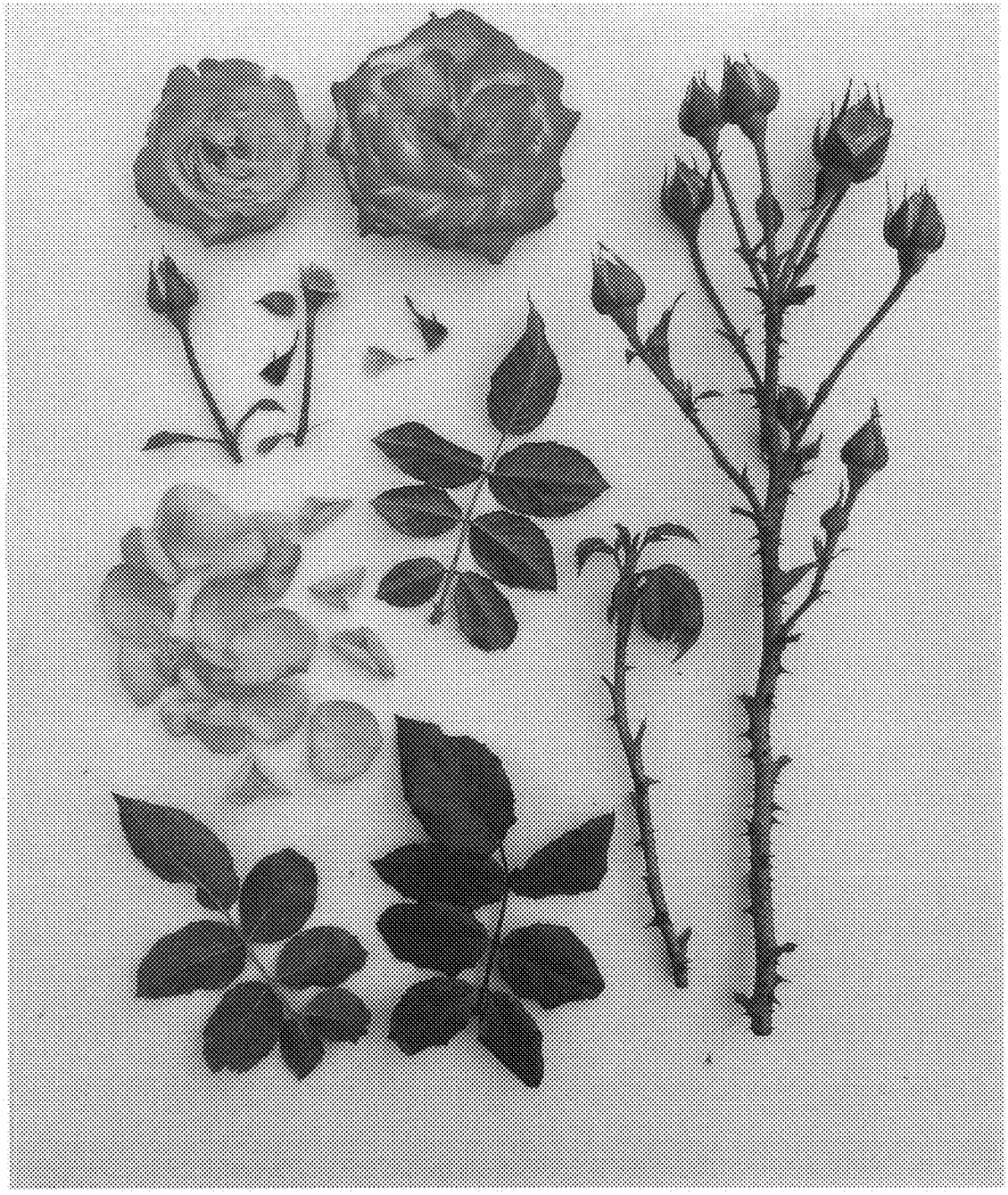

* * * * *